United States Patent
Tal et al.

(10) Patent No.: US 10,617,850 B2
(45) Date of Patent: Apr. 14, 2020

(54) BALLOON CATHETER WITH FORTIFIED PROXIMAL OUTLET PORT, AND MANUFACTURING THEREOF

(71) Applicant: A.V. Medical Technologies LTD, Tel-Aviv (IL)

(72) Inventors: Michael Gabriel Tal, Savyon (IL); Gil Bernstein, Qiryat Ono (IL); Limor Sandach, Tel-Aviv (IL)

(73) Assignee: Covidien LP, Mansfield, MA (US)

( * ) Notice: Subject to any disclaimer, the term of this patent is extended or adjusted under 35 U.S.C. 154(b) by 194 days.

(21) Appl. No.: 15/738,742

(22) PCT Filed: Jun. 26, 2016

(86) PCT No.: PCT/IB2016/053804
§ 371 (c)(1),
(2) Date: Dec. 21, 2017

(87) PCT Pub. No.: WO2016/207865
PCT Pub. Date: Dec. 29, 2016

(65) Prior Publication Data
US 2018/0177983 A1     Jun. 28, 2018

Related U.S. Application Data

(60) Provisional application No. 62/184,536, filed on Jun. 25, 2015.

(51) Int. Cl.
*A61M 25/10* (2013.01)
*A61M 25/00* (2006.01)
(Continued)

(52) U.S. Cl.
CPC ............ *A61M 25/10* (2013.01); *A61L 29/02* (2013.01); *A61L 29/04* (2013.01); *A61M 5/007* (2013.01);
(Continued)

(58) Field of Classification Search
CPC .. A61M 2025/1097; A61M 2025/0037; A61M 2025/105; A61M 2025/1052;
(Continued)

(56) References Cited

U.S. PATENT DOCUMENTS

| 4,585,000 A | 4/1986 | Hershenson |
| 4,794,928 A | 1/1989 | Kletschka |

(Continued)

FOREIGN PATENT DOCUMENTS

| EP | 0770405 A2 | 5/1997 |
| WO | 9402196 A1 | 2/1994 |

(Continued)

OTHER PUBLICATIONS

Besarab et al "Catheter Management in Hemodialysis Patients: Delivering Adequate Flow". Clinical Journal of the American Society of Nephrology. vol. 6 (2011): 227-234.

(Continued)

*Primary Examiner* — Bhisma Mehta
*Assistant Examiner* — Nilay J Shah
(74) *Attorney, Agent, or Firm* — Carter, DeLuca & Farrell LLP

(57) ABSTRACT

Infusion balloon catheter with fortified proximal infusion outlet port, and manufacturing thereof. Infusion balloon catheter includes: inflatable balloon member; shaft having distal end attached to balloon member, and shaft wall enclosing: first lumen providing passage to balloon inflation fluid, and second lumen providing passage to infusion fluid and guidewire; and bending-resistant insert member housed in second lumen and located proximally to balloon member, insert member is affixed to, and conforms to shape of, shaft inner wall surface, and includes one or more openings(s). Shaft wall has infusion outlet port located along, and providing opening to, second lumen proximally to balloon (Continued)

member. Insert opening(s) is/are in direct fluid communication with infusion outlet port whose cross-sectional area is larger than that of infusion inlet opening. Bending-resistant insert member provides fortifying structural support to shaft wall portion surrounding infusion outlet port. Applicable to medical procedures involving injection of imaging contrast material or/and drugs.

23 Claims, 6 Drawing Sheets

(51) Int. Cl.
  *A61L 29/02* (2006.01)
  *A61L 29/04* (2006.01)
  *A61M 5/00* (2006.01)

(52) U.S. Cl.
  CPC ...... *A61M 25/007* (2013.01); *A61M 25/0026* (2013.01); *A61M 25/0052* (2013.01); *A61M 25/1036* (2013.01); *A61M 25/0028* (2013.01); *A61M 25/0029* (2013.01); *A61M 2025/0037* (2013.01); *A61M 2025/0039* (2013.01); *A61M 2025/0073* (2013.01); *A61M 2025/105* (2013.01); *A61M 2025/1052* (2013.01); *A61M 2025/1061* (2013.01); *A61M 2025/1084* (2013.01)

(58) Field of Classification Search
  CPC .. A61M 2025/1061; A61M 2025/1084; A61M 25/0028; A61M 25/10; A61M 25/005; A61M 25/0052; A61M 25/0026; A61M 25/0029; A61M 25/007; A61M 25/1036; A61M 2025/0039; A61M 25/0102; A61M 2025/0073
  See application file for complete search history.

(56) References Cited

U.S. PATENT DOCUMENTS

| | | | |
|---|---|---|---|
| 5,069,673 A | | 12/1991 | Shwab |
| 5,250,038 A | * | 10/1993 | Melker ............ A61M 25/0032 604/167.01 |
| 5,267,979 A | | 12/1993 | Appling et al. |
| 5,306,247 A | | 4/1994 | Pfenninger |
| 5,318,032 A | | 6/1994 | Lonsbury et al. |
| 5,344,402 A | * | 9/1994 | Crocker ............ A61M 25/1011 604/103.01 |
| 5,368,567 A | | 11/1994 | Lee |
| 5,439,447 A | † | 8/1995 | Miraki |
| 5,693,088 A | | 12/1997 | Lazarus |
| 5,836,967 A | | 11/1998 | Schneider |
| 5,908,407 A | | 6/1999 | Frazee |
| 6,010,521 A | | 1/2000 | Lee et al. |
| 6,017,323 A | | 1/2000 | Chee |
| 6,022,336 A | | 2/2000 | Zadno-azizi |
| 6,051,020 A | | 4/2000 | Goicoechea et al. |
| 6,231,543 B1 | | 5/2001 | Hegde et al. |
| 6,440,097 B1 | | 8/2002 | Kupiecki |
| 6,485,500 B1 | | 11/2002 | Kokish et al. |
| 6,544,217 B1 | | 4/2003 | Gulachenski |
| 6,663,648 B1 | † | 12/2003 | Trotta |
| 7,182,755 B2 | | 2/2007 | Tal |
| 7,195,611 B1 | | 3/2007 | Simpson et al. |
| 7,873,404 B1 | | 1/2011 | Patton |
| 8,532,749 B1 | † | 9/2013 | Patton |
| 9,931,492 B2 | | 4/2018 | Sarradon |
| 2002/0143251 A1 | | 10/2002 | Richardson et al. |
| 2003/0204236 A1 | | 10/2003 | Letort |
| 2004/0068250 A1 | | 4/2004 | Boutilette |
| 2004/0116832 A1 | | 6/2004 | Friedrich et al. |
| 2004/0122465 A1 | | 6/2004 | McMurtry et al. |
| 2006/0064058 A1 | | 3/2006 | Coyle |
| 2006/0253071 A1 | | 11/2006 | Zattera |
| 2007/0060882 A1 | | 3/2007 | Tal |
| 2007/0129752 A1 | | 6/2007 | Webler |
| 2008/0221550 A1 | | 9/2008 | Lee |
| 2009/0312827 A1 | | 12/2009 | Stapleton |
| 2010/0025606 A1 | | 2/2010 | Hoppe |
| 2010/0198186 A1 | | 8/2010 | Ackermann |
| 2011/0270373 A1 | | 11/2011 | Sampognaro et al. |
| 2012/0265135 A1 | | 10/2012 | Porter |
| 2012/0265287 A1 | | 10/2012 | Sharma |
| 2013/0172661 A1 | | 7/2013 | Farnan et al. |
| 2014/0316263 A1 | | 10/2014 | Murphy |
| 2015/0209557 A1 | | 7/2015 | Tal et al. |
| 2016/0013597 A1 | | 1/2016 | Huang |

FOREIGN PATENT DOCUMENTS

| | | |
|---|---|---|
| WO | 9505862 A1 | 3/1995 |
| WO | 9942059 A2 | 8/1999 |
| WO | 0156645 A1 | 8/2001 |
| WO | 2012110598 A1 | 8/2012 |
| WO | 2014009809 A1 | 1/2014 |
| WO | 2014113257 A2 | 7/2014 |
| WO | 2015104631 A1 | 7/2015 |

OTHER PUBLICATIONS

Hacker et al "Fibrin Sheath Angioplasty: A Technique to Prevent Superior Vena Cava Stenosis Secondary to Dialysis Catheters". The International Journal of Angiology: Official Publication of the International College of Angiology, Inc. 21-3 (2012): 129-134.

Oct. 13, 2016 International Search Report issued in International Application No. PCT/IB2016/053804.

\* cited by examiner
† cited by third party

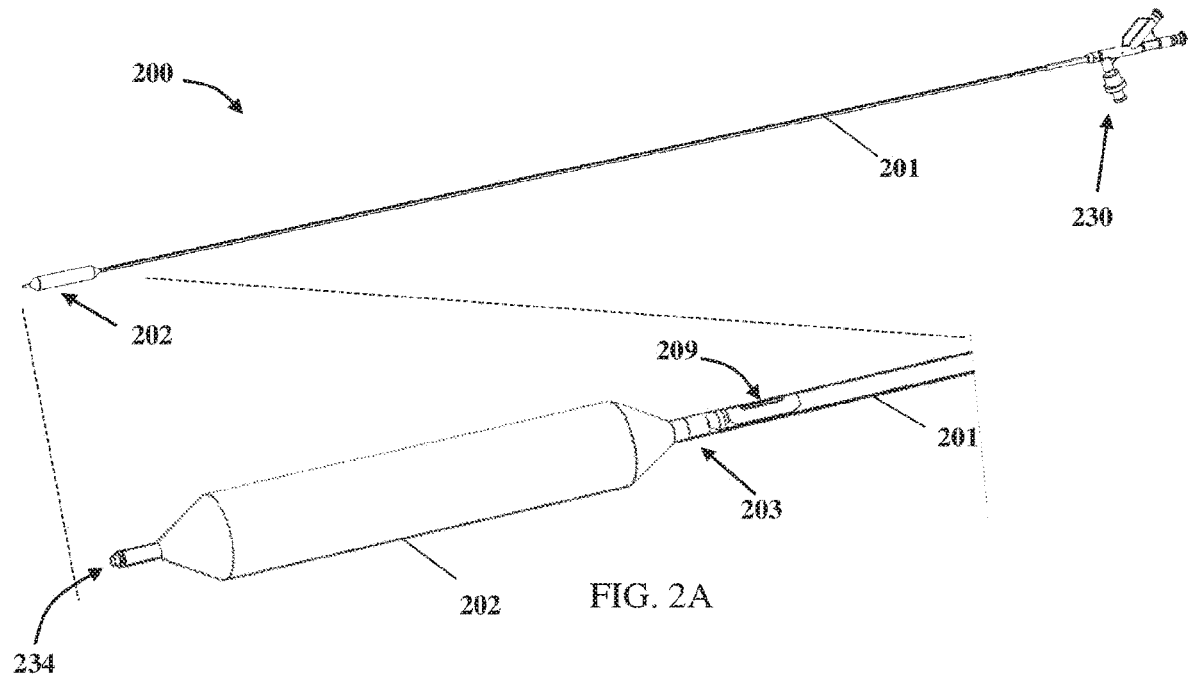
FIG. 2A
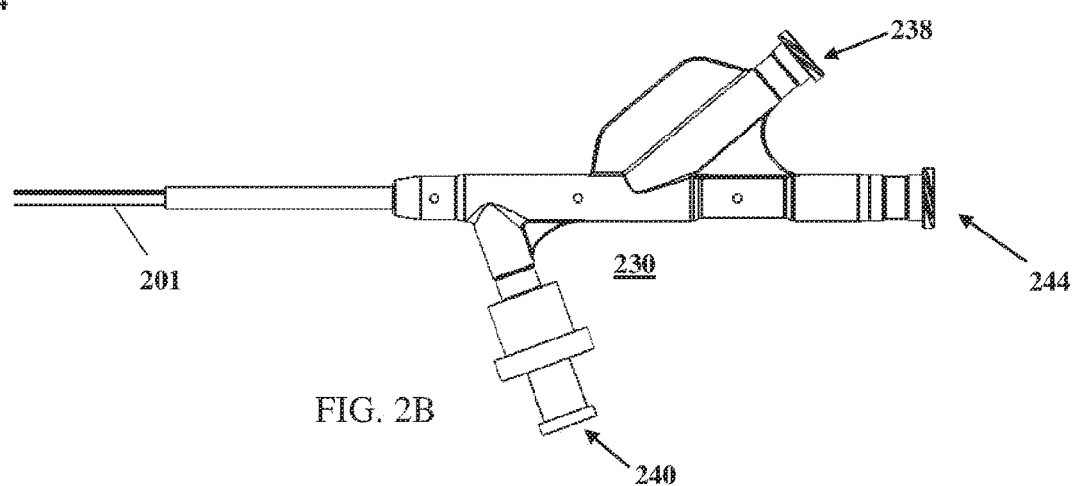
FIG. 2B
FIG. 2C
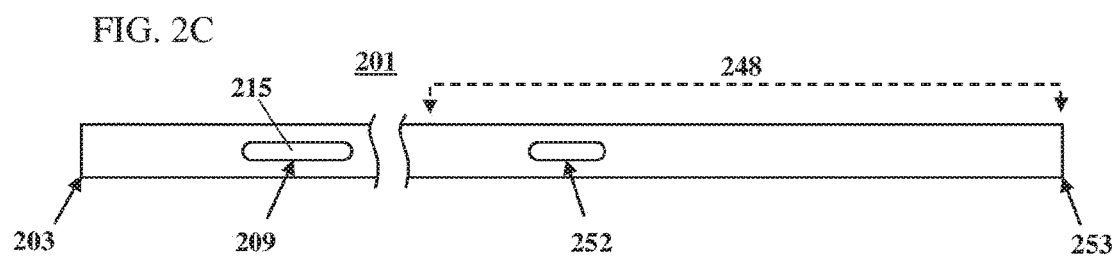

500      FIG. 5

*{Manufacturing an infusion balloon catheter.}*

504

Providing a multi-lumen shaft having a shaft wall enclosing at least a first lumen and a second lumen separated, and separately sealed, from each other by a dividing wall.

508

Forming an infusion outlet port in proximity to a distal end of the shaft.

512

Inserting into second lumen a bending-resistant insert member having at least one insert opening, the bending-resistant insert member conforms to shape of inner surface of the shaft wall with each lateral end thereof extending to a junction line of the dividing wall and the shaft wall, thereby preventing rotation of the bending-resistant insert member in the second lumen.

516

Shifting the bending-resistant insert member into coincidence with the infusion outlet port, such that the at least one insert opening is in direct fluid communication with the infusion outlet port at a seam formed via the coincidence.

520

Affixing the bending-resistant insert member to the shaft wall, so as to prevent or minimize relative movement or shifting between the at least one insert opening and the infusion outlet port.

BALLOON CATHETER WITH FORTIFIED PROXIMAL OUTLET PORT, AND MANUFACTURING THEREOF

RELATED APPLICATION

This application is a U.S. National Stage Entry Under 35 U.S.C. 371 of International Application No. PCT/IB2016/053804 filed on Jun. 26, 2016, which claims the benefit of priority under 35 USC 119(e) of U.S. Provisional Patent Application No. 62/184,536, filed Jun. 25, 2015, entitled "BALLOON CATHETER WITH FORTIFIED PROXIMAL INFUSION OUTLET PORT". The contents of the above applications are incorporated herein by reference in their entireties.

FIELD OF THE INVENTION

The present invention, in some embodiments thereof, relates to infusion balloon catheters, and more particularly, but not exclusively, to an infusion balloon catheter with fortified (strengthened) proximal infusion outlet port, and a method of manufacturing thereof. Some embodiments of the invention are particularly suitable for use in applications of, or relating to, dialysis procedures that involve injecting imaging contrast material into the blood stream of a subject.

BACKGROUND OF THE INVENTION

Injections of imaging contrast material during dialysis related procedures is usually performed manually using a standard syringe, with evidence suggesting optimal results have correlation with ease of injection (especially, injection force applied by the physician) and amount of imaging contrast material injected within a short period of time. Based on such evidences, current techniques are based on using standard angiographic infusion catheters for peripheral and arteriovenous (AV) access that have a single infusion opening located at the catheter distal tip, which commonly provide high quality angiographic and imaging results. Recently, there has been motivation to develop infusion balloon catheters with a single side hole, or with a plurality of side holes, provided proximally to the balloon member of the catheter. The main justification for that is to allow localized low-dose injection of imaging contrast material (usually, in the same direction as blood flow) against the proximal periphery of the inflated and expanded balloon member of the infusion catheter.

Currently know forms of side hole infusion balloon catheters, employed using standard injection parameters, may be considered prone to produce jets generally directed toward blood vessel walls. Production of such jets, instead of streamlined injection, of imaging contrast material within the blood flow can lead to undesirable and disadvantageous effects such as of creating local turbulence, which results in immediate dilution of imaging contrast material within the blood. Such result is accompanied by decreasing imaging contrast quality, instead of locally replacing blood with contrast material that provides high density of local imaging contrast material. Another disadvantage of having jet producing side openings in infusion balloon catheters may be the inherent risk in potentially damaging blood vessels, especially, small blood vessels. Multiple or/and narrow jets aimed at blood vessel walls may cause perforation or dissection of wall tissue, especially, in blood vessels damaged either by disease or by recent intervention or manipulation.

Another difficulty that may arise during catheter infusions is the resistance to flow of infusion material, such as of imaging contrast material. The small cross-sectional area, long travel through the infusion lumen, together with, at times, insufficient mechanical advantage produced by the injecting apparatus (syringe prefilled with the contrast media), affects such resistance to flow.

In view of at least the preceding disadvantages and limitations associated with currently known and used infusion balloon catheters, there is an on-going need for developing and implementing new and improved infusion balloon catheters, along with corresponding methods of manufacturing such catheters.

SUMMARY OF THE INVENTION the present invention, in some embodiments thereof, relates to infusion balloon catheters, and more particularly, but not exclusively, to an infusion balloon catheter with fortified (strengthened) infusion outlet port, and a method of manufacturing thereof. Some of these or other embodiments, particularly relate to infusion balloon catheters possessing a sufficiently enlarged infusion outlet port for diminishing resistance to flow. Some of these or other embodiments particularly relate to balloon infusion catheters having their infusion outlet port positioned proximally to the balloon member they carry. Some embodiments of the invention are particularly suitable for use in applications of, or relating to, dialysis procedures that involve injecting imaging contrast material into the blood stream of a subject.

By implementing a substantially enlarged opening proximally and in approximation to the balloon member, the catheter shaft section encompassing this opening will suffer substantial loss of structural integrity, making it prone to bending and kinking, especially during forceful pushing in small vessels. Some embodiments of the present invention provide an infusion balloon catheter with a fortified catheter shaft about the infusion outlet port thereof. In some such embodiments, the infusion balloon catheter includes an inflation lumen directed to selectively inflate the balloon member, and a separate infusion lumen directed to selectively infusion fluids such as imaging contrast material or/and a pharmaceutical (drug) agent. The inherent asymmetry in cross section of a multi-lumen catheter shaft may further escalate random yielding (e.g., kinking, bending, or twisting) of the shaft about the enlarged opening created at the shaft wall section covering the infusion lumen only, leaving the adjacent shaft wall covering the inflation lumen intact.

In exemplary embodiments, the infusion balloon catheter includes a bending-resistant insert member housed in one of two or more separated, and separately sealed, catheter lumens and is located proximally to a balloon member attached to the distal end of a catheter shaft. The bending-resistant insert member is affixed to, and conforms to the shape of, the inner surface of the catheter shaft wall encompassing the infusion lumen, and includes at least one insert opening enabling outflow of infusion fluid. The catheter shaft wall has an infusion outlet port, including one or more infusion openings, located along, and providing opening to, the infusion lumen proximally to the balloon member. The at least one insert opening(s) is in direct fluid communication with the infusion outlet port. In some embodiments, at least one through hole, formed through the at least one insert opening and the infusion outlet port, has a cross-sectional area greater by at least 0.5 mm$^2$ than an effective infusion lumen cross-sectional area. In some embodiments, the through hole cross-sectional area is equal to or greater than the maximal cross-sectional area in the entire passage the infusion fluid passed until reaching the opening. The bending-resistant insert member provides fortifying structural support to the catheter shaft wall portion surrounding the infusion outlet port. The herein disclosed infusion balloon catheter is readily connectable to a multi-connector that is configured for delivery devices (syringes, guidewire, etc.) being connected thereto.

In exemplary embodiments, the method of manufacturing the infusion balloon catheter includes the step/procedure of inserting, into in one of two or more separated, and separately sealed, catheter lumens, a bending-resistant insert member having at least one insert opening. The bending-resistant insert member conforms to the shape of the inner surface of the catheter shaft wall, with each lateral end of the bending-resistant insert extending to a junction line of a multi-lumen dividing wall and the catheter shaft wall, thereby preventing rotation of the bending-resistant insert member inside its surrounding lumen. An infusion outlet port is formed in proximity to the catheter shaft distal end, and there is shifting the bending-resistant insert member into coincidence with the infusion outlet port, such that the at least one insert opening is in direct fluid communication with the infusion outlet port. The at least one insert opening and the infusion outlet port have similar shape and dimensions at a seam formed via the coincidence. The method further includes affixing the bending-resistant insert member to the catheter shaft wall encompassing the infusion lumen, so as to prevent or minimize relative movement or shifting between the at least one insert opening and the infusion outlet port of the catheter.

According to an aspect of some embodiments of the present invention, there is provided an infusion balloon catheter comprising: an inflatable balloon member; a shaft whose distal end is attached to the balloon member, and having a shaft wall enclosing: a first lumen that provides passage to a balloon inflation fluid, and a second lumen that provides passage to an infusion fluid and a guidewire; and a bending-resistant insert member housed in the second lumen and located proximally to the balloon member, the bending-resistant insert member is affixed to, and conforms to shape of, inner surface of the shaft wall, and includes at least one insert opening; the shaft wall has an infusion outlet port located along, and providing an opening to, the second lumen proximally to the balloon member, the at least one insert opening is in direct fluid communication with the infusion outlet port, and the bending-resistant insert member provides structural support to a portion of the shaft wall surrounding the infusion outlet port.

According to some embodiments of the invention, the bending-resistant insert member provides structural support along a length extending between a point in proximity to proximal end of the infusion outlet port and a point in proximity to proximal end of the balloon member.

According to some embodiments of the invention, the first and second lumens are separated, and separately sealed, from each other by a dividing wall extending along length of the shaft, such that the balloon inflation fluid passing through the first lumen is separated from the infusion fluid passing through the second lumen. According to some embodiments of the invention, one of the first and second lumens has an oval shaped cross section, and other of the first and second lumens has a crescent shaped cross section.

According to some embodiments of the invention, the bending-resistant insert member has lateral ends protruding away from the inset opening towards the dividing wall.

According to some embodiments of the invention, the bending-resistant insert member abuts the inner surface of the shaft wall along most or all perimeter thereof spanning between the lateral ends thereof. According to some embodiments of the invention, each lateral end is adjacent to, or in contact with, a corresponding junction line of the dividing wall with the shaft wall, thereby holding the bending-resistant insert member in the second lumen so as to prevent rotation of the bending-resistant member around long axis of the shaft.

According to some embodiments of the invention, the bending-resistant insert member is housed in a dedicated section of the second lumen bordered with slide-prevention elements that prevent the bending-resistant insert member from proximally or distally sliding along length of the shaft. According to some embodiments of the invention, at least one of the slide-prevention elements is formed by local constriction of the inner surface of the shaft wall. According to some embodiments of the invention, at least one of the slide-prevention elements is an end portion of a tube lain at least partially across the second lumen.

According to some embodiments of the invention, the bending-resistant insert member is configured as a plate member made from at least one material selected from: stainless steel, aluminum, Co—Cr alloy, Ni—Ti alloy, and hard polymer. According to some embodiments of the invention, the bending-resistant insert member has a length of at least 5 mm. According to some embodiments of the invention, the bending-resistant insert member has a thickness of at least 0.03 mm.

According to some embodiments of the invention, the bending-resistant insert member includes at least one elastically deformable portion, being elastically deformable from a first non-stressed shape to a second stressed shape. According to some embodiments of the invention, the bending-resistant insert member includes at least one less bending-resistant portion, being less resistant to bending relative to other portions of the bending-resistant insert member, thereby allowing the bending-resistant insert member to bend about the at least one less bending-resistant portion, while relieving bending stresses that form in the other portions. According to some embodiments of the invention, the at least one less bending-resistant portion includes a joint member, a gap, or/and a slit.

According to some embodiments of the invention, the at least one insert opening has a minimal cross sectional dimension of less than 0.7 mm. According to some embodiments of the invention, the shaft has an outer diameter of 2 mm or less. According to some embodiments of the invention, the bending-resistant insert member is curved in accordance with a portion of the shape of the inner surface of the shaft wall.

According to some embodiments of the invention, the at least one insert opening and the infusion outlet port are sized, shaped, or/and arranged to thereby direct flow of the infusion fluid distally via an obtuse angle. According to some embodiments of the invention, the obtuse angle is 110 degrees or more. According to some embodiments of the invention, the obtuse angle is 130 degrees or more. According to some embodiments of the invention, the at least one insert opening and the infusion outlet port are sized, shaped, or/and arranged to thereby direct an infusion fluid outflow having a flow rate in a range of between about 1 $cm^3$/sec and about 2 $cm^3$/sec. According to some embodiments of the invention, the at least one insert opening is juxtaposed with the infusion outlet port. According to some embodiments of the invention, the at least one insert opening is larger than the infusion outlet port, or, optionally, smaller than the infusion outlet port.

According to some embodiments of the invention, the infusion outlet port includes a single infusion opening. According to some embodiments of the invention, the infusion opening has a largest cross sectional dimension of at least 2 mm. According to some embodiments of the invention, the infusion opening has a smallest cross sectional dimension of 1 mm or less. According to some embodiments of the invention, the infusion outlet port includes a plurality of infusion openings. According to some embodiments of the invention, a center point of the infusion outlet port is located 25 mm or less proximally to the closest point of the balloon member.

According to some embodiments of the invention, at least one through hole, formed through the at least one insert opening and the infusion outlet port, has a cross-sectional area greater by at least 0.5 mm$^2$ than an effective infusion lumen cross-sectional area. According to some embodiments of the invention, the effective infusion lumen cross-sectional area is equal to or smaller than a minimum cross-sectional area of the infusion lumen proximally to the infusion outlet port, minus at least about 0.385 mm$^2$. According to some embodiments of the invention, the at least one through hole has a cross-sectional area equal to or greater than 2 mm$^2$. According to some embodiments of the invention, the at least one through hole has a cross-sectional area greater than cross-sectional area of an infusion inlet opening provided at a proximal end of the shaft wall and configured for direct fluid communication with an infusion fluid delivery apparatus. According to some embodiments of the invention, the at least one through hole cross-sectional area is at least 1.5 times greater than cross-sectional area of the infusion inlet opening. According to some embodiments of the invention, the at least one through hole cross-sectional area is greater by at least 0.85 mm$^2$ than cross-sectional area of the infusion inlet opening.

According to an aspect of some embodiments of the present invention, there is provided a method of manufacturing an infusion balloon catheter, the method comprising: providing a multi-lumen shaft having a shaft wall enclosing at least a first lumen and a second lumen separated, and separately sealed, from each other by a dividing wall; forming an infusion outlet port in proximity to a distal end of the shaft; inserting into the second lumen a bending-resistant insert member having at least one insert opening, the bending-resistant insert member conforms to shape of inner surface of the shaft wall with each lateral end thereof extending to a junction line of the dividing wall and the shaft wall, thereby preventing rotation of the bending-resistant insert member in the second lumen; shifting the bending-resistant insert member into coincidence with the infusion outlet port, such that the at least one insert opening is in direct fluid communication with the infusion outlet port at a seam formed via the coincidence; and affixing the bending-resistant insert member to the shaft wall, so as to prevent or minimize relative movement or shifting between the at least one insert opening and the infusion outlet port.

According to some embodiments of the invention, the affixing includes forming a proximal slide-prevention element adjacently proximal to the bending-resistant insert member and a distal slide-prevention element adjacently distal to the bending-resistant insert member, thereby preventing or minimizing axial motion of the bending-resistant insert member in the second lumen. According to some embodiments of the invention, the affixing includes bonding the bending-resistant insert member to an inner surface of the shaft wall with a bonding agent. According to some embodiments of the invention, the bending-resistant insert member is coated with the bonding agent prior to the bonding.

According to some embodiments of the invention, the manufacturing method further comprises connecting a balloon assembly, including an inflatable balloon member, to the distal end of the shaft. According to some embodiments of the invention, the balloon assembly includes an inner tube configured for passing a guidewire, and connecting the balloon assembly facilitates holding a proximal end of the inner tube extending in, and distally to, the second lumen, the inner tube proximal end is positioned and sized so as to prevent or minimize distal shifting of the bending-resistant insert member from the coincidence.

According to some embodiments of the invention, the manufacturing method further comprises adding a heat shrink element about the shaft wall proximally to the bending-resistant insert member, so as to prevent or minimize proximal shifting of the bending-resistant insert member from the coincidence.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, by firmware, or a combination thereof, using an operating system.

BRIEF DESCRIPTION OF THE SEVERAL
VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

Figure 1A:
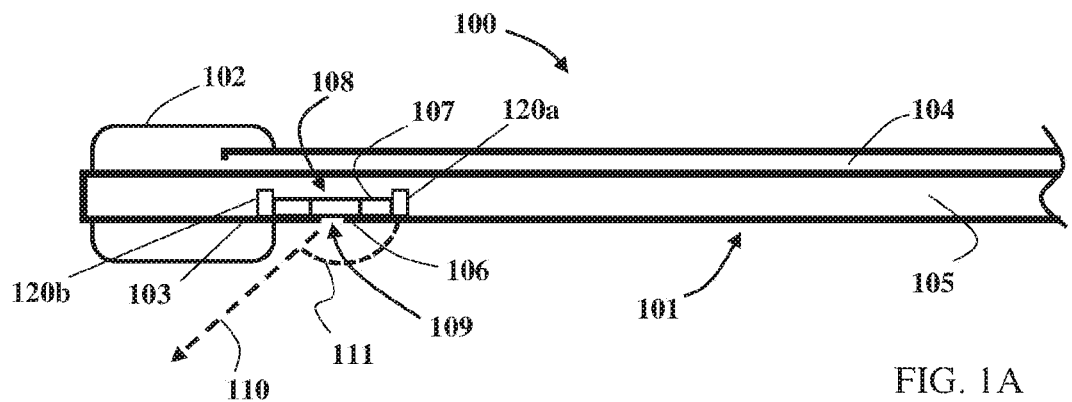
FIG. 1A is a schematic side cut view of an exemplary infusion balloon catheter with a fortified proximal infusion outlet port, highlighting a bending-resistant insert member housed in one of two separated, and separately sealed, catheter lumens, and located proximally to a balloon member attached to the catheter shaft distal end, in accordance with some embodiments of the invention.
Figure 1B:
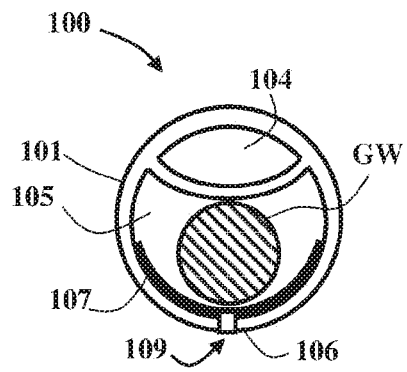
FIGS. 1B and 1C are schematic cross sectional views of the exemplary infusion balloon catheter of FIG. 1A about the fortified portion thereof, with an exemplary guidewire provided in the infusion lumen and without a guidewire in the infusion lumen, respectively, in accordance with some embodiments of the invention.
Figure 1C:
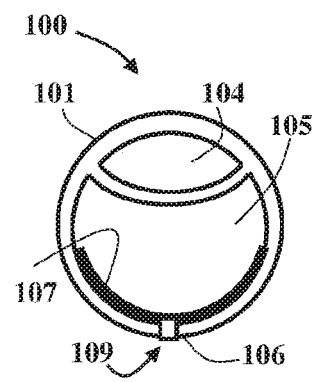
Figure 1D:
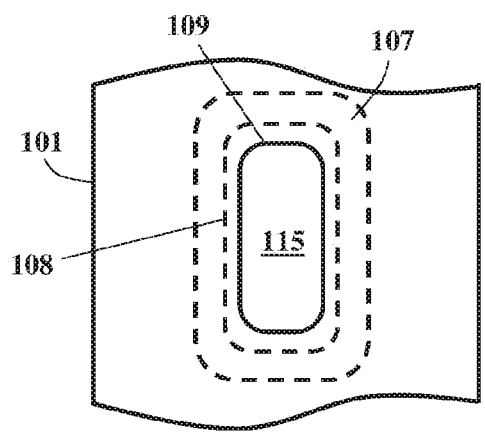
Figure 1E:
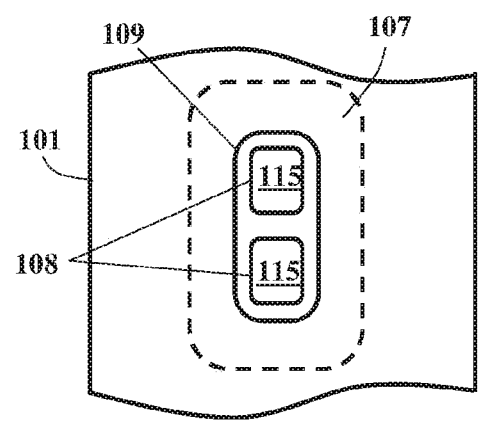
Figure 2D:
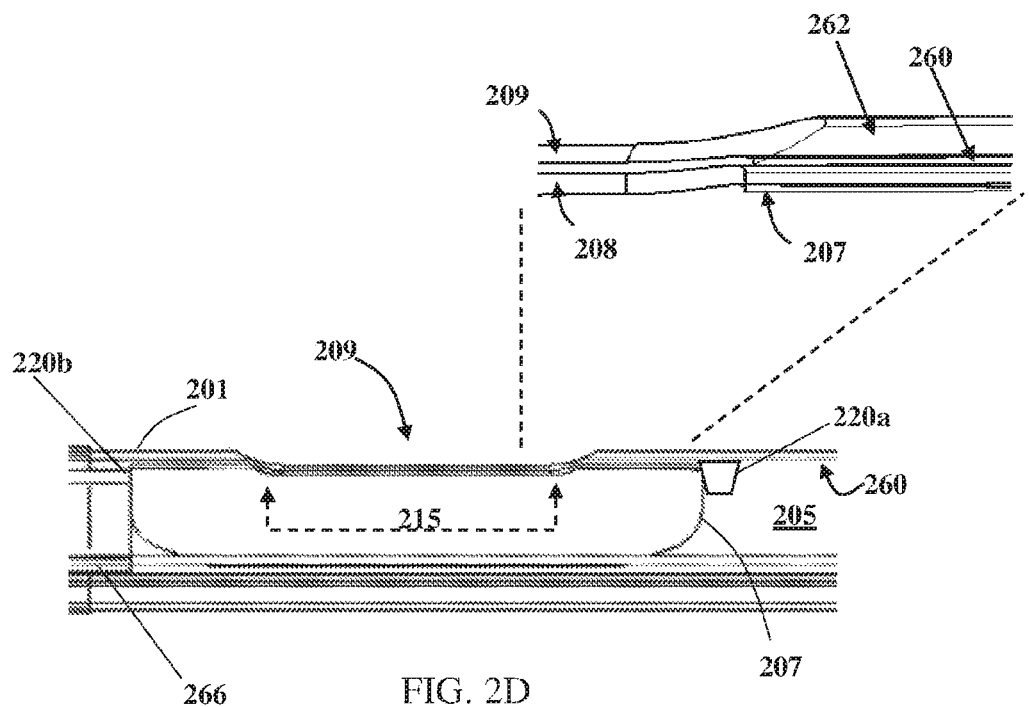
Figure 2E:
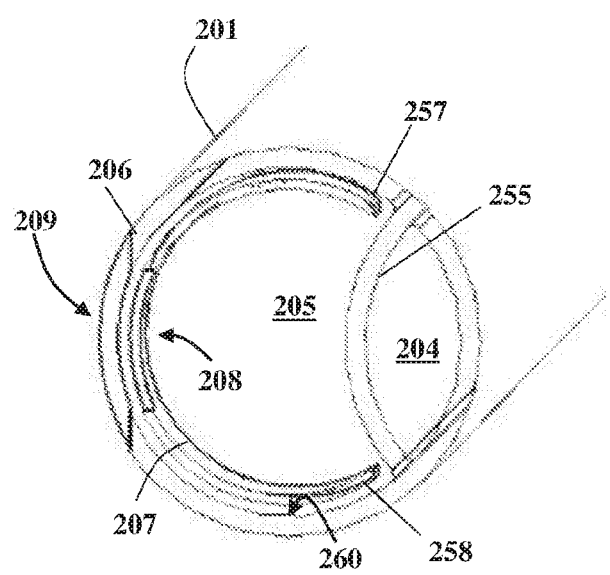
Figure 2F:
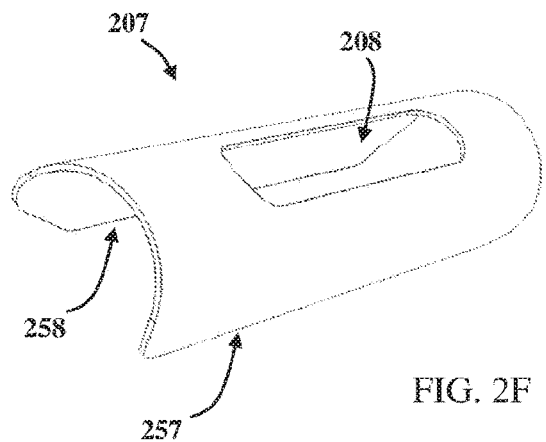
Figure 2G:
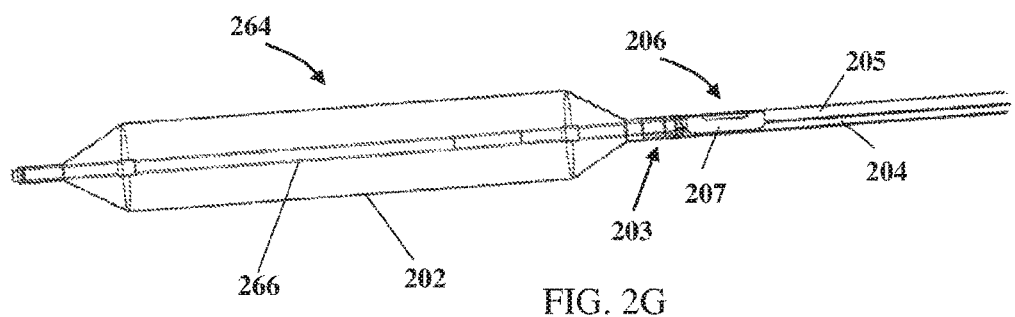
Figure 2H:
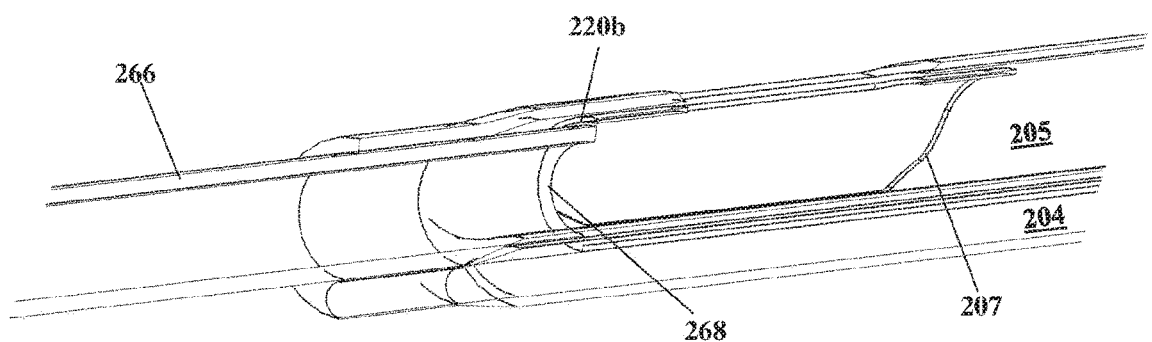
Figure 4A:
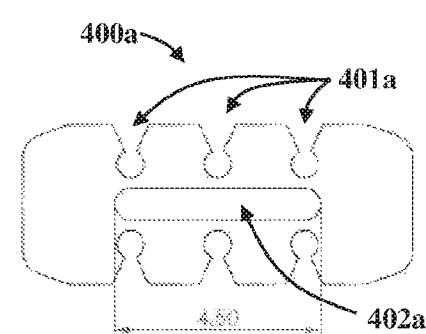
Figure 4B:
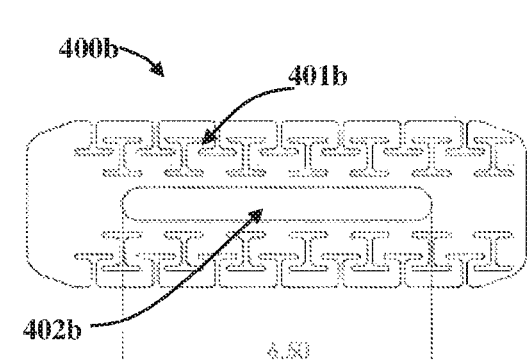

FIGS. 1D and 1E are schematic top sectional views of the exemplary infusion balloon catheter of FIG. 1A about the fortified portion thereof, highlighting exemplary embodiments of a single through hole (FIG. 1D) formed through a single insert opening and the infusion outlet port, and of two through holes (FIG. 1E) formed through two insert openings and the infusion outlet port, in accordance with some embodiments of the invention;

FIG. 2A is a schematic perspective close-up view of the distal portion of an exemplary infusion balloon catheter (similar to or same as that of FIG. 1A), also showing connection thereof to the distal end of an exemplary multi-connector assembly, in accordance with some embodiments of the invention;

FIG. 2B is a schematic side view of a proximal portion of the herein disclosed exemplary infusion balloon catheter connected to the exemplary multi-connector assembly of FIG. 2A, in turn, configured for delivery devices (syringes, guidewire, etc.) being connected thereto, in accordance with some embodiments of the invention;

FIG. 2C is a schematic diagram illustrating an exemplary catheter shaft section inside the exemplary multi-connector assembly of FIGS. 2A and 2B relative to the distal portion of the exemplary infusion balloon catheter of FIG. 2A (similar to or same as that of FIG. 1A), highlighting an exemplary infusion opening (of an infusion outlet port) and an exemplary fluid inlet opening (for injecting infusion fluid into the infusion lumen), and exemplary dimensions thereof, in accordance with some embodiments of the invention;

FIG. 2D is a side cut view of the distal end portion of an exemplary infusion balloon catheter (similar to or same as that of FIG. 1A), highlighting an exemplary bending-resistant insert member housed inside the catheter infusion lumen, along with a close-up perspective view of exemplary structural features thereof, in accordance with some embodiments of the invention;

FIG. 2E is a perspective cut view of the distal end portion shown in FIG. 2D, highlighting exemplary relative configurations and locations/positions of components and features of the exemplary bending-resistant insert member housed inside the catheter infusion lumen, in accordance with some embodiments of the invention;

FIG. 2F is a schematic perspective view of an exemplary bending-resistant insert member having an exemplary single insert opening, and included in the exemplary infusion balloon catheter of FIGS. 2A-2E, in accordance with some embodiments of the invention;

FIG. 2G is a perspective side cut view of the distal portion of the exemplary infusion balloon catheter of FIG. 2A, highlighting an exemplary balloon assembly connected thereto, in accordance with some embodiments of the invention;

FIG. 2H is a perspective side cut close-up view of the infusion lumen distal end shown housing part of the bending-resistant insert member, and of the inflation lumen distal end relative thereto, highlighting a transparent inner view of an exemplary balloon assembly with inner tube, balloon member, and catheter shaft distal end, in accordance with some embodiments of the invention;

FIGS. 3A-3F are schematic top views of several bending-resistant insert members, suitable for inclusion in exemplary embodiments of the infusion balloon catheter, highlighting various different exemplary forms or configurations and numbers of insert openings therein, in accordance with some embodiments of the invention;

FIGS. 4A and 4B are schematic top views of two exemplary bending-resistant insert members, suitable for inclusion in exemplary embodiments of the infusion balloon catheter, highlighting different exemplary forms or configurations and numbers of less bending-resistant portions, being less resistant to bending relative to other portions of the bending-resistant insert member, in accordance with some embodiments of the invention; and FIG. 5 is a flow diagram of exemplary steps (procedures/processes) of an exemplary method of manufacturing an infusion balloon catheter (such as that shown in the preceding figures), in accordance with some embodiments of the invention.

DESCRIPTION OF SPECIFIC EMBODIMENTS OF THE INVENTION

The present invention, in some embodiments thereof, relates to infusion balloon catheters, and more particularly, but not exclusively, to an infusion balloon catheter with fortified (strengthened) infusion outlet port, and a method of manufacturing thereof. Some of these or other embodiments, particularly relate to infusion balloon catheters possessing a sufficiently enlarged infusion outlet port for diminishing resistance to flow. Some of these or other embodiments particularly relate to balloon infusion catheters having their infusion outlet port positioned proximally to the balloon member they carry. Some embodiments of the invention are particularly suitable for use in applications of, or relating to, dialysis procedures that involve injecting imaging contrast material into the blood stream of a subject.

By implementing a substantially enlarged opening proximally and in approximation to the balloon member, the catheter shaft section encompassing this opening will suffer substantial loss of structural integrity, making it prone to bending and kinking, especially during forceful pushing in small vessels. Some embodiments of the present invention provide an infusion balloon catheter with a fortified catheter shaft about the infusion outlet port thereof. In some such embodiments, the infusion balloon catheter includes an inflation lumen directed to selectively inflate the balloon member, and a separate infusion lumen directed to selectively infusion fluids such as imaging contrast material or/and a pharmaceutical (drug) agent. The inherent asymmetry in cross section of a multi-lumen catheter shaft may further escalate random yielding (e.g., kinking, bending, or twisting) of the shaft about the enlarged opening created at the shaft wall section covering the infusion lumen only, leaving the adjacent shaft wall covering the inflation lumen intact.

In exemplary embodiments, the infusion balloon catheter includes a bending-resistant insert member housed in one of two or more separated, and separately sealed, catheter lumens and is located proximally to a balloon member attached to the distal end of a catheter shaft. The bending-resistant insert member is affixed to, and conforms to the shape of, the inner surface of the catheter shaft wall encompassing the infusion lumen, and includes at least one insert opening enabling outflow of infusion fluid. The catheter shaft wall has an infusion outlet port, including one or more infusion openings, located along, and providing opening to, the infusion lumen proximally to the balloon member. The at least one insert opening(s) is in direct fluid communication with the infusion outlet port. In some embodiments, at least one through hole, formed through the at least one insert opening and the infusion outlet port has a cross-sectional area greater by at least 0.5 mm$^2$ than an effective infusion lumen cross-sectional area. In some embodiments, the through hole cross-sectional area is equal to or greater than the maximal cross-sectional area in the entire passage the infusion fluid passed until reaching the opening. The bending-resistant insert member provides fortifying structural support to the catheter shaft wall portion surrounding the infusion outlet port. The herein disclosed infusion balloon catheter is readily connectable to a multi-connector that is configured for delivery devices (syringes, guidewire, etc.) being connected thereto.

In exemplary embodiments, the method of manufacturing the infusion balloon catheter includes the step/procedure of inserting, into in one of two or more separated, and separately sealed, catheter lumens, a bending-resistant insert member having at least one insert opening. The bending-resistant insert member conforms to the shape of the inner surface of the catheter shaft wall, with each lateral end of the bending-resistant insert extending to a junction line of a multi-lumen dividing wall and the catheter shaft wall, thereby preventing rotation of the bending-resistant insert member inside its surrounding lumen. An infusion outlet port is formed in proximity to the catheter shaft distal end, and there is shifting the bending-resistant insert member into coincidence with the infusion outlet port, such that the at least one insert opening is in direct fluid communication with the infusion outlet port. The at least one insert opening and the infusion outlet port have similar shape and dimensions at a seam formed via the coincidence. The method further includes affixing the bending-resistant insert member to the catheter shaft wall encompassing the infusion lumen, so as to prevent or minimize relative movement or shifting between the at least one insert opening and the infusion outlet port of the catheter.

As explained in the Background section, currently known forms of side hole infusion balloon catheters, employed using standard injection parameters, are prone to produce jets generally directed toward blood vessel walls. Production of such jets, instead of streamlined injection, of imaging contrast material within the blood flow typically creates local turbulence, which results in immediate dilution of imaging contrast material within the blood, thereby decreasing imaging contrast quality, instead of locally replacing blood with contrast material that provides high density of local imaging contrast material. Such jet producing side openings in infusion balloon catheters may also present inherent risk in potentially damaging blood vessels, especially, small blood vessels.

Prior art includes teachings about designing side hole infusion balloon catheters, particularly, for infusion of pharmaceutical agents, that focus on means for delivering minute quantities of fluid locally to blood vessel walls using jets or diffusion. Such teachings may be limited, or even disadvantageous, for application to medical procedures involving injections of imaging contrast material, for example, by substantially limiting rates and overall quantities of imaging contrast material injectable into a subject's blood stream. The inventors observed that there may be need in such medical procedures to have the capability of delivering a relatively substantial quantity of imaging contrast material (e.g., 1 cc [cm$^3$, ml] to 5 cc [cm$^3$, ml]) within a short time period (e.g., 1 to 3 seconds), without causing jets or other turbulent effects in the subjects's blood vessels.

In view of at least the herein described possible limitations and disadvantages associated with current infusion balloon catheters having jet-producing side-holes, the inventors of the present invention conceived of, designed, developed, and reduced to practice, exemplary embodiments of an infusion balloon catheter with fortified proximal infusion outlet port, and a method of manufacturing thereof. In exemplary embodiments, the infusion balloon catheter has a relatively substantially large sized (side located) infusion outlet port (with one or more openings), for example, having a cross-sectional area of at least 1 mm$^2$, or at least 2 mm$^2$, or at least 3 mm$^2$, or at least 4 mm$^2$. In some embodiments, the infusion outlet port includes a single, relatively long and narrow, opening, extending along catheter shaft axis, optionally about 0.5 mm to about 1 mm, optionally about 0.7 mm wide, and optionally about 3 mm to about 5 mm, optionally about 4 mm, long. Such a relatively large sized infusion outlet port, under normal manual injection characteristics (e.g., applied force and injection pressure), prevents or minimizes jet creation, and minimizes resistance to manual injection from the catheter and its surroundings, along with maintaining, or even increasing, rates and quantities of imaging contrast material deliverable into the hosting blood vessel.

Introducing one or more large sized (side located) infusion openings, especially, if these are located immediately proximally to a catheter balloon member, will increase probability for bending, kinking, or collapsing of the catheter shaft within a subject's body, in a way that can damage the catheter form and function, as well as putting a patient at risk of internal injury. Collapsing of a catheter shaft may happen during catheter insertion into a subject's body through a vascular sheath or/and over a guide wire, or when advancing it through a stenosis or an occlusion under resistance. In order to avoid the risk of bending, kinking, or collapsing of the catheter shaft about a relatively large sized (side located) infusion outlet port (and opening(s)), the inventors conceived of, designed, developed, and reduced to practice, exemplary embodiments of means to fortify (strengthen) catheter shaft portions surrounding the infusion outlet port (and opening(s)), while maintaining efficient overall catheter dimensions, including external shaft dimensions and inner lumen(s) dimensions.

Some exemplary embodiments of the present invention relate to maintaining catheter shaft flexibility similar to that exhibited by currently employed infusion balloon catheters, so as to enable proper catheter maneuverability within blood vessels. Accordingly, in exemplary embodiments, herein disclosed catheter infusion outlet port fortifying (strengthening) means are designed and constructed so as to cause no, or minimal, reduction in overall catheter shaft flexibility.

In exemplary embodiments of the present invention, in an effort to improve areal efficiency in catheter lumen design, a same lumen is configured and functions with the capability to deliver different means or facilitators associated with different functionalities of the infusion balloon catheter. For example, a single lumen within the catheter shaft is configured and functions for proximal injection/infusion of a fluid via an infusion outlet port (e.g., having one or more infusion openings) provided proximally to the balloon member, and also for passing a guidewire therethrough across the entire length of the catheter shaft and of the balloon member. In such exemplary embodiments, the proximally located infusion outlet port or/and the fortifying (strengthening) means have shape and dimensions that prevent a guidewire passing therethrough, while directing the guidewire towards a dedicated guidewire opening (in the same lumen) provided distally to the balloon member.

Devices, assemblies, sub-assemblies, mechanisms, structures, components, elements, parameters, dimensions, configurations, equipment, accessories, and materials, and, steps or procedures, sub-steps or sub-procedures, as well as operation and implementation, of exemplary embodiments, alternative embodiments, specific configurations, and, additional and optional aspects, characteristics, or features, thereof, of some embodiments of the present invention, are better understood with reference to the following illustrative description and accompanying drawings. Throughout the following illustrative description and accompanying drawings, same reference notation and terminology (i.e., numbers, letters, symbols) are consistently used and refer to same structures, components, elements, steps or procedures, or/and features. It is to be understood that the invention is not necessarily limited in its application to particular details of construction or/and arrangement of device or apparatus components, or to particular sequential ordering of method steps or procedures, set forth in the following illustrative description. The invention is capable of other embodiments or of being practiced or carried out in various ways.

The phrase 'bending-resistant insert member', as used herein, refers to an insert member having (exhibiting) mechanical properties and characteristics which substantially resist (prevent) bending of the insert member, or alternatively stated, enable the insert member to substantially resist (prevent) from being bent. In exemplary embodiments, such mechanical characteristics may also substantially resist (prevent) kinking, curling, or/and twisting, of the insert member, or alternatively stated, enable the insert member to substantially resist (prevent) from being kinked, curled, or/and twisted. In a particular exemplary embodiment, the 'bending-resistant insert member' may be considered as being substantially rigid, thereby having (exhibiting) rigidity type mechanical and physicochemical properties and characteristics.

The phrase 'less bending-resistant portion', as used herein, refers to a portion of the herein disclosed bending-resistant insert member being less resistant (i.e., having less resistance) to bending relative to other portions of the bending-resistant insert member.

An aspect of some embodiments of the present invention is an infusion balloon catheter.

FIG. 1A is a schematic side cut view of an exemplary infusion balloon catheter 100 with a fortified proximal infusion outlet port 106, highlighting a bending-resistant insert member 107 housed in an infusion lumen 105 separated, and separately sealed, from an inflation lumen 104, and located proximally to a balloon member 102 attached to the catheter shaft distal end 103. FIGS. 1B and 1C are schematic cross sectional views of the exemplary infusion balloon catheter 100 of FIG. 1A about the fortified portion thereof, with an exemplary guidewire GW provided in the infusion lumen 105, and without a guidewire in the infusion lumen 105, respectively. FIGS. 1D and 1E are schematic top sectional views of the exemplary infusion balloon catheter of FIG. 1A about the fortified portion thereof, highlighting exemplary embodiments of a single through hole (FIG. 1D) formed through a single insert opening and the infusion outlet port, and of two through holes (FIG. 1E) formed through two insert openings and the infusion outlet port.

In exemplary embodiments, and as shown in FIGS. 1A-1E, infusion balloon catheter 100 includes: an inflatable balloon member 102; a shaft 101 whose distal end 103 is attached to balloon member 102, and having a shaft wall enclosing: a first lumen (e.g., an inflation lumen) 104 that provides passage to a balloon inflation fluid, and a second lumen (e.g., an infusion lumen) 105 that provides passage to an infusion fluid and a guidewire GW; and a bending-resistant insert member 107 housed in the second lumen 105 and located proximally to the balloon member 102, wherein the bending-resistant insert member 107 is affixed to, and conforms to shape of, the inner surface of the wall of shaft 101, and includes at least one insert opening 108.

As shown, in exemplary embodiments, infusion balloon catheter 100 includes catheter shaft 101 attached to inflatable balloon member 102 at a distal end 103 thereof. The wall of shaft 101 has an infusion outlet port 106 located along, and providing an opening to, the second lumen 105 proximally to the balloon member 102. The at least one insert opening 108 is in direct fluid communication with the infusion outlet port 106. The bending-resistant insert member 107 provides (fortification type) structural support to a portion of the wall of shaft 101 surrounding the infusion outlet port 106.

Infusion balloon catheter 100 may be of any size or/and type, for example, a dilatation type infusion balloon catheter or/and a micro-catheter having a shaft diameter being 3 mm or less, optionally, 2 mm or less, or optionally, 1 mm or less. Balloon member 102 may be designated as compliant, semi-compliant or non-compliant, and intended for dilatation or/and occlusions of blood vessel segment. Shaft 101 encloses inflation lumen 104 and infusion lumen 105 that are separated, and sealed, from each other. Inflation lumen 104 is opened to inner boundaries of balloon member 102. Infusion lumen 105 is opened to an infusion outlet port 106 provided proximally to balloon member 102. Infusion outlet port 106 (in a center point thereof) is located 25 mm or less proximally to a closest point of balloon member 102, optionally, about 15 mm or less, or optionally, about 6 mm or less. In the illustrated exemplary embodiment, infusion outlet port 106 includes a single infusion opening 109, although in other exemplary embodiments, infusion outlet port 106 may include a plurality of, for example, same or differently configured, shaped, sized, or/and dimensioned, infusion openings 109.

Bending-resisting insert member 107, provided inside infusion lumen 105, includes at least one insert opening 108, and is fixedly coupled to shaft 101. As shown in this example, bending-resistant insert member 107 is affixed to, and conforms to the (curved) shape of, the inner surface of the wall of shaft 101, and includes at least one insert opening 108. The at least one insert opening 108 and the infusion outlet port 106 are juxtapositionally arranged, and together form at least one through hole (for example, 115 shown in FIGS. 1D, 1E; and 215 shown in FIGS. 2C, 2E), thereby allowing infusion fluid to pass therethrough and outside of the shaft 101. In exemplary embodiments, the at least one through hole 115 or 215 has a cross-sectional area greater by at least 0.5 mm$^2$ than an effective infusion lumen cross-sectional area, which may be considered, in some embodiments of the present invention, as the remaining cross sectional area derived from subtracting guidewire GW cross-sectional area from total cross-sectional area of infusion lumen 105. Therefore, when the guidewire GW is in place, the infusion fluid can flow only in a passage formed between the guidewire and the inner surface surrounding the infusion lumen, until exiting at the infusion outlet port 106 via through hole(s) 115.

FIG. 1D shows an exemplary single through hole 115 as formed by combination (i.e., juxtapositional arrangement) of an exemplary single insert opening 108 of bending-resistant insert member 107 and an exemplary single infusion opening 109 of infusion outlet port 106. FIG. 1E shows two exemplary through holes 115 as formed by combination (juxtapositional arrangement) of two exemplary insert openings 108 and the single infusion opening 109 of infusion outlet port 106.

In exemplary embodiments, the at least one insert opening(s) 108, the infusion outlet port 106 (and its one or more infusion openings 109), and the resulting through hole 115 are shaped, sized, or/and arranged, to provide for one or more of the following infusion properties and characteristics:

Resistance to manual operation (e.g., finger/thumb pressing) of a syringe supplying imaging contrast material is minimal, so that any additional force required for injecting imaging contrast material via infusion lumen 105 (also if housing guidewire GW therein) and through hole 115 is significantly small, in order not to be particularly recognized or sensed by the operator. In exemplary embodiments, force required for plunger breakforce (i.e., the force required to initiate plunger movement) and for flushing is about 10 lbs or less, optionally, about 5 lbs or less, or optionally, about 3 lbs or less (for example, when using a luer-lock type 10 cc [ml] syringe filled with a mixture containing 50% normal saline solution and 50% iodinated imaging contrast material).

Maximal flow rate of imaging contrast material injected via infusion outlet port 106 is substantially higher than current commercially available infusion balloon catheters. In exemplary embodiments, recommended imaging contrast material infusion flow rates are about 1 cc [ml]/sec or higher, optionally, about 1.3 cc [ml]/sec or higher, or optionally, about 1.5 cc [ml]/sec or higher (for example, when using a luer-lock type 10 cc [ml] syringe filled with a mixture containing 50% normal saline solution and 50% iodinated imaging contrast material).

Imaging contrast material stream infused via infusion outlet port 106 submerges within blood flow in a streamlined fashion or/and without causing significant turbulence (for example, when using a luer-lock type 10 cc [ml] syringe filled with a mixture containing 50% normal saline solution and 50% iodinated imaging contrast material).

Angle of injected stream via infusion outlet ports 106 (relative to catheter shaft axis and directed distally) is substantially greater than 90 degrees, in order to minimize impact and load to adjacent blood vessel walls. In exemplary embodiments, flow angle through infusion port outlet 106 is about 110 degrees or more, optionally, about 120 degrees or more, optionally, about 130 degrees or more, or optionally, about 140 degrees to about 150 degrees (for example, when using a luer-lock type 10 cc [ml] syringe filled with a mixture containing 50% normal saline solution and 50% iodinated imaging contrast material).

Possible guidewire infiltration is prevented, by limiting at least one dimension (e.g., opening width, length, or/and diameter) to be smaller than the diameter of guidewire GW. For example, minimal dimension (e.g., width) of insert opening 108 is 1 mm or less, optionally, about 0.7 mm or less, optionally, about 0.5 mm or less.

Reference is additionally made to FIGS. 2A-2H, which, together with FIGS. 1A-1E, further illustrate several exemplary embodiments of the herein disclosed infusion balloon catheter, and, components, technical features, and characteristics thereof.

FIG. 2A is a schematic perspective close-up view of the distal portion of an exemplary infusion balloon catheter 200 (similar to or same as exemplary infusion balloon catheter 100 shown in FIG. 1A), also showing connection thereof to the distal end of an exemplary multi-connector assembly 230. In exemplary embodiments, multi-connector assembly 230 is a 3× luer-lock type multi-connector. FIG. 2B is a schematic side view of a proximal portion of the herein disclosed exemplary infusion balloon catheter 200 connected, via shaft 201, to the exemplary multi-connector assembly 230, in turn, configured for delivery devices (syringes, guidewire, etc.) being connected thereto. As shown therein, the distal end of multi-connector assembly 230 is connected, at the distal end 203 of shaft 201, to a balloon assembly that includes an inflatable balloon member 202. Distal end of inflatable balloon member 202 is configured with a guidewire distal port 234. FIG. 2A shows an exemplary location of insert opening 206 relative to distal end 203 of catheter shaft 201 and proximal end of inflatable balloon member 202. As shown in FIG. 2B, multi-connector assembly 230 includes an inflation fluid inlet port 238 (optionally connectable to a syringe which can be filled with saline solution), an infusion fluid inlet port 240 (optionally connectable to a syringe filled with contrast enhancing fluid), and a guidewire proximal port 244 (which can be used for inserting, passing or/and removing a guidewire), and is connected to the proximal end of catheter shaft 201.

FIG. 2C is a schematic diagram illustrating shaft 201 extending between shaft distal end 203 and shaft proximal end 253, and focuses, particularly, to an exemplary catheter shaft section 248 inside the exemplary multi-connector assembly 230 of FIGS. 2A and 2B relative to the distal portion of the exemplary infusion balloon catheter 200 of FIG. 2A (similar to or same as infusion balloon catheter 100 of FIG. 1A), highlighting an exemplary through hole 215, an exemplary infusion opening 209 (of infusion outlet port 206), and an exemplary fluid inlet opening 252 (which communicates directly with infusion fluid inlet port 240, for injecting infusion fluid into the infusion lumen), and exemplary dimensions thereof. In exemplary embodiments, infusion opening 209 (of infusion outlet port 206) has a length dimension of 4 mm and a width dimension of 0.7 mm, while infusion fluid inlet opening 252 has a length dimension of 2.6 mm and a width dimension of 0.7 mm. Such an exemplary embodiment shows the size dimensions of infusion opening (of infusion outlet port 206) being substantially larger than size dimensions of infusion inlet opening 252.

FIG. 2D is a side cut view of the distal end portion of shaft 201, highlighting an exemplary bending-resistant insert member 207 housed inside catheter infusion lumen 205, along with a close-up perspective view of exemplary structural features thereof. FIG. 2E is a perspective cut view of the distal end portion shown in FIG. 2D, highlighting exemplary relative configurations and locations/positions of components and features of the exemplary bending-resistant insert member 207 housed inside the catheter infusion lumen 205. FIG. 2G is a perspective side cut view of the distal portion of shaft 201, highlighting an exemplary balloon assembly 264 connected thereto. FIG. 2H is a perspective side cut close-up view of the distal end portion of shaft 201 shown housing part of bending-resistant insert member 207, and of the inflation lumen 204 distal end relative thereto, highlighting a transparent inner view of exemplary balloon assembly 264 with inner tube 266, balloon member 202, and catheter shaft distal end 203. Inner tube 266 is sized and configured to allow a guidewire (such as guidewire GW shown in FIG. 2B) passing therethrough across length of balloon member 202. In some embodiments, inner tube 206 is sized to accurately fit or snugly fit outer dimensions of a prescribed guidewire (e.g., a 0.35" diameter guidewire), such that infusion infiltration distally to infusion outlet port 206 and into inner tube 266 is diminished or prevented, when a guidewire is housed thereinside.

In exemplary embodiments, bending-resistant insert member 207 provides (fortification type) structural support along a length extending between a point in proximity to the proximal end of infusion outlet port 206 and a point in proximity to the proximal end of balloon member 202. In exemplary embodiments, first lumen (inflation lumen) 204 and second lumen (infusion lumen) 205 are separated, and separately sealed, from each other by a dividing wall 255 extending along length of shaft 201, such that balloon inflation fluid passing through first lumen 204 is separated from infusion fluid passing through second lumen 205.

In exemplary embodiments, one of first and second lumens 204 and 205, respectively, has an oval or lens shaped cross section (in this example, first lumen 204), and the other of first and second lumens 204 and 205, respectively, has a crescent shaped cross section (in this example, second lumen 205). In exemplary embodiments, bending-resistant insert member 207 has lateral ends 257 and 258 (also shown in FIG. 2F) protruding away from inset opening 208 towards the dividing wall 255. In exemplary embodiments, bending-resistant insert member 207 abuts the inner wall surface (e.g., inner wall surface 260 shown in FIGS. 2D and 2E) of the catheter shaft 201 along most or all of the perimeter thereof spanning between lateral ends 257 and 258. In exemplary embodiments, each of the lateral ends 257 and 258 is adjacent to, or in contact with, a corresponding junction line of dividing wall 255 with the shaft wall 262 of shaft 201, thereby holding bending-resistant insert member 207 in second lumen 205 so as to prevent rotation of bending-resistant member 207 around the long axis of the catheter shaft 201.

In exemplary embodiments, bending-resistant insert member 207 is housed in a dedicated section of second lumen 205 bordered with slide-prevention elements (e.g., 120a and 120b shown in FIG. 1A; 220a shown in FIG. 2D) that prevent bending-resistant insert member 207 from proximally or distally sliding along the length of the shaft 201. In exemplary embodiments, a proximal slide-prevention element 220a is formed by local constriction of the inner surface 260 of shaft wall 262. In exemplary embodiments, a distal slide-prevention element 220b is an end portion 268 of inner tube 266 lain at least partially across second lumen 205. Optionally, bending-resistant insert member 207 is further bonded to at least one of proximal and distal slide-prevention elements, 220a and 220b, respectively.

FIG. 2F is a schematic perspective view of an exemplary bending-resistant insert member 207 having an exemplary single insert opening 208, and included in the exemplary infusion balloon catheter of FIGS. 2A-2E. In some embodiments, bending-resistant insert member 207 is curved in accordance with the inner surface 260 and boundaries of a wall portion of a designated host balloon catheter shaft 201, such that it can fortify shaft portions around infusion outlet port 206. In some embodiments, bending-resistant insert member 207 is formed of stainless steel 304 alloy, and is optionally, about 0.65 mm in thickness and about 7 mm in length, curved as an arc shape in cross section as a portion of a tube being 1.64 mm in outer diameter. In exemplary embodiments, bending-resistant insert member 207 includes at least one elastically deformable portion, whereby such portion is elastically deformable from a first non-stressed shape to a second stressed shape. In exemplary embodiments, insert opening 208 is oval shaped having a maximum length of about 4 mm and a width of about 0.7 mm, with a total cross-sectional area of about 2.7 mm$^2$. In exemplary embodiments, infusion outlet port 206 has an infusion opening 209 whose size and shape are the same as those of insert opening 208.

In exemplary embodiments, bending-resistant insert member 207 is configured as a plate member made from at least one material selected from: stainless steel, aluminum, Co—Cr alloy, Ni—Ti alloy, and hard polymer. In exemplary embodiments, bending-resistant insert member 207 has a length of at least 5 mm. In exemplary embodiments, bending-resistant insert member 207 has a thickness of at least 0.03 mm. In exemplary embodiments, bending-resistant insert member 207 includes at least one elastically deformable portion, being elastically deformable from a first non-stressed shape to a second stressed shape. For example, such an elastically deformable portion is made from a piece or segment of hot worked metal or/and of metal having spring or spring-like properties and characteristics.

In exemplary embodiments, bending-resistant insert member 207 includes at least one less bending-resistant portion, being less resistant to bending relative to other portions of bending-resistant insert member 207, thereby allowing bending-resistant insert member 207 to bend about at least one less bending-resistant portion while relieving bending stresses that form in other portions. In exemplary embodiments, at least one less bending-resistant portion includes a joint member, a gap, or/and a slit. Examples of such exemplary embodiments of bending-resistant insert member 207 including a plurality of less bending-resistant portions are further illustratively described hereinbelow, with reference to FIGS. 4A and 4B.

In exemplary embodiments, at least one insert opening 208 has a minimal cross sectional dimension of less than 0.7 mm. In exemplary embodiments, shaft 201 has an outer diameter of 2 mm or less. In exemplary embodiments, bending-resistant insert member 207 is curved in accordance with a portion of the shape of the inner surface 260 of shaft wall 262.

In exemplary embodiments, the at least one insert openings 208 and the infusion outlet port 206 including its at least one infusion opening 209, are sized, shaped, or/and arranged to thereby direct flow of infusion fluid distally via an obtuse angle. In exemplary embodiments, the obtuse angle is 110 degrees or more, or, optionally, 130 degrees or more (relative to catheter shaft axis, directed distally). In exemplary embodiments, the at least one insert opening 208 and the infusion fluid outlet port 206 including its at least one infusion opening 209 are sized, shaped, or/and arranged to thereby direct an infusion fluid outflow having a flow rate in a range of between about 0.5 cm$^3$/sec and about 2 cm$^3$/sec, optionally, in a range of between about 1.0 cm$^3$/sec and about 2.0 cm$^3$/sec, optionally, in a range of between about 1.0 cm$^3$/sec and about 1.5 cm$^3$/sec.

In exemplary embodiments, at least one insert opening 208 is juxtaposed with infusion outlet port 206 including its at least one infusion opening 209. In exemplary embodiments, at least one insert opening 208 is larger than, or smaller than, infusion outlet port 206.

In exemplary embodiments, infusion outlet port 206 includes a single infusion opening, for example, infusion opening 209. In exemplary embodiments, infusion opening 209 has a largest cross sectional dimension (width or length) of at least 2 mm. In exemplary embodiments, infusion opening 209 has a smallest cross sectional dimension (width or length) of 1 mm or less. In exemplary embodiments, infusion outlet port 206 includes a plurality of infusion openings 209. In exemplary embodiments, a center point of infusion outlet port 206 is located 25 mm or less proximally to closest point of balloon member 202.

In exemplary embodiments, at least one through hole 215, formed through the at least one insert opening 208 and the infusion outlet port 206, is 1 mm or less, optionally, in width or/and in length thereof, optionally, the smallest between width and length thereof. In exemplary embodiments, the at least one through hole 215 has a cross-sectional area greater by at least 0.5 mm$^2$ than an effective infusion lumen cross-sectional area. In exemplary embodiments, the effective infusion lumen cross-sectional area is equal to or smaller than a minimum cross-sectional area of infusion lumen 205 proximally to infusion outlet port 206, minus at least about 0.3 mm$^2$, optionally at least about 0.385 mm$^2$. In exemplary embodiments, the at least one through hole 215 has a cross-sectional area equal to or greater than 2 mm$^2$. In exemplary embodiments, the at least one through hole 215 has a cross-sectional area greater than cross-sectional area of an infusion inlet opening (e.g., 252 shown in FIG. 2C) provided at a shaft proximal end 253 and configured for direct fluid communication with an infusion fluid delivery apparatus (for example, multi-connector delivery apparatus 230 shown in FIGS. 2A and 2B). In exemplary embodiments, the at least one through hole cross-sectional area is at least 1.5 times greater than the cross-sectional area of the infusion fluid inlet opening 252. In exemplary embodiments, the at least one through hole cross-sectional area is greater by at least 0.85 mm$^2$ than the cross-sectional area of the infusion fluid inlet opening 252.

In some embodiments, insert opening 208 (or each of a plurality of insert openings) includes a minimal cross-sectional dimension less than about 1 mm, optionally, about 0.7 mm or less, so that guidewire GW, being 0.889 mm (0.035″) in diameter, in this example, will be prevented from passing therethrough.

In some embodiments, the through hole 215 has a cross-sectional area equal to or greater than an effective cross-sectional area of the infusion lumen 205, where, for example, the latter includes the total infusion lumen cross-sectional area minus the guidewire GW cross-sectional area when provided in the infusion lumen 205 during an infusion process (e.g., delivery of infusion fluid such as contrast medium or/and medication). In some embodiments, the through hole 215 has a cross-sectional area at least about 0.3%, or optionally, at least about 0.5%, or equal to, or greater than, the cross-sectional area of a syringe tip opening used for exemplary infusion balloon catheter 200 (for example, a commercially available luer-lock type 10 cc [ml] syringe has tip opening of about 4.3 mm$^2$). Optionally, the through hole 215 has a cross-sectional area equal to or greater than about 2 mm$^2$, or optionally, equal to or greater than about 4 mm$^2$.

The following table (Table 1) presents test results of measuring infusion fluid flow rates and flow angles as a function of insert opening size dimensions, when using infusion balloon catheters similar in form and dimensions to exemplary infusion balloon catheter 200, yet differentiated by dimensions of insert opening thereof.

TABLE 1

Infusion fluid flow rate (cc[ml]/sec) and flow angle (degrees) as a function of insert opening size dimensions.

| Insert opening length (oval) mm | Insert opening width (oval) mm | Insert opening cross section mm$^2$ | Flow rate cc[ml]/sec | Flow angle degrees |
|---|---|---|---|---|
| 2.6 | 0.6 | 1.48 | 1.33 | 112.72 |
| 4 | 0.7 | 2.69 | 1.45 | 120.48 |
| 4.5 | 0.7 | 3.00 | 1.47 | 125.46 |
| 5 | 0.7 | 3.39 | 1.49 | 127.99 |
| 5.5 | 0.7 | 3.74 | 1.50 | 135.27 |
| 6 | 0.7 | 4.09 | 1.52 | 140.51 |
| 6.5 | 0.7 | 4.44 | 1.52 | 153.15 |

Results shown in Table 1 were obtained using a luer-lock type 10 cc [ml] syringe. Flow angle was determined using pure water as infusion material at high-pressure injection. Flow rate was determined using a mixture containing about 50% normal saline and about 50% iodinated imaging contrast material, at an injection pressure of about 2 bar.

FIGS. 3A-3F are schematic top views of several exemplary bending-resistant insert members, suitable for inclusion in exemplary embodiments of the infusion balloon catheter (e.g., 100 or 200), highlighting various different exemplary forms or configurations and numbers of insert openings therein. A particular design and configuration of the insert opening or/and the number of insert openings (e.g., 108 or 208) in a single bending-resistant insert member (e.g., 107 or 207) may be preferred where strengthening of the proximal infusion outlet port (e.g., 106 or 206) should be maintained or increased while keeping or decreasing other strength related variables, such as insert material, thickness, among others. Size, shape, number, or/and distribution, of insert openings may be considered also in relation to desired flow characteristics of the infusion fluid (e.g., flow rate or/and pressure).

Figure 3A:
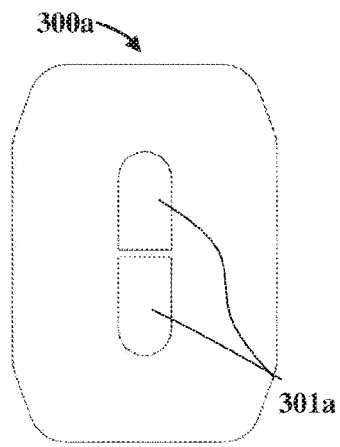
Figure 3B:
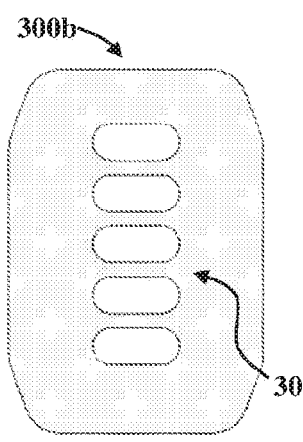
Figure 3C:
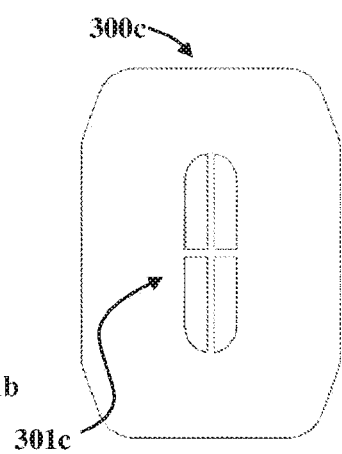
Figure 3D:
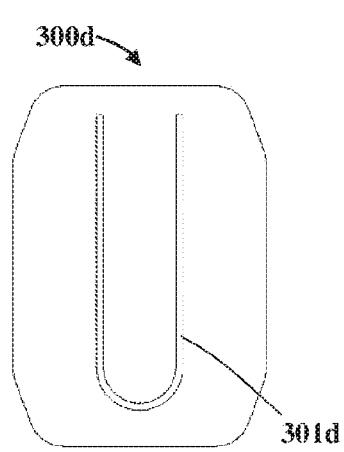
Figure 3E:
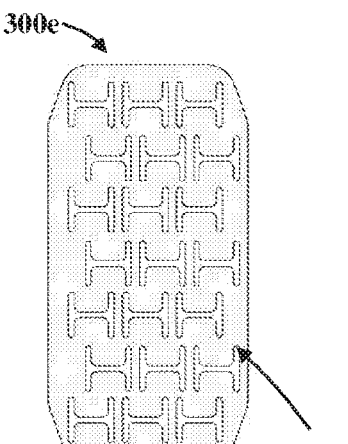
Figure 3F:
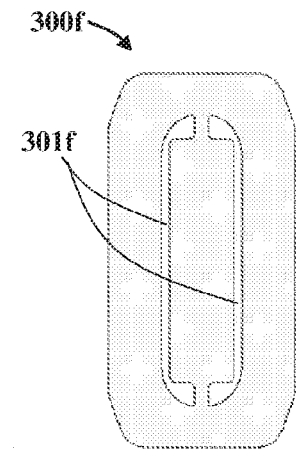

FIG. 3A shows an exemplary bending-resistant insert member 300a having two adjacent longitudinally distributed insert openings 301a. FIG. 3B shows an exemplary bending-resistant insert member 300b having five adjacent longitudinally distributed insert openings 301b. FIG. 3C shows an exemplary bending-resistant insert member 300c having a rectangular cluster of four adjacent insert openings 301c. FIG. 3D shows an exemplary bending-resistant insert member 300d having a single U-shaped insert opening 301d. FIG. 3E shows an exemplary bending-resistant insert member 300e having a cluster of 21 adjacent H-shaped insert openings 301e distributed throughout the surface area of bending-resistant insert member 300e. FIG. 3F shows an exemplary bending-resistant insert member 300f having two opposing and mirrored C-shaped insert openings 301f.

In exemplary embodiments, the bending-resistant insert member (e.g., 107 or 207) for fortifying the proximal infusion outlet port (e.g., 106 or 206) includes at least one bending portion being less bending-resistant relative to other bending-resistant portions of the overall bending-resistant insert member (107 or 207). Such embodiments provide for controlled bending of the bending-resistant member (107 or 207) about at least one of the less bending-resistant portions, while relieving bending stresses from the bending resisting portions thereof.

FIGS. 4A and 4B are schematic top views of two exemplary bending-resistant insert members 400a and 400b, respectively, suitable for inclusion in exemplary embodiments of the infusion balloon catheter (100 or 200), highlighting different exemplary forms or configurations and numbers of less bending-resistant portions, being less resistant to bending relative to other portions of the bending-resistant insert member (400a or 400b). FIG. 4A shows a bending-resistant insert member 400a having a number of shaped cuts and gaps 401a distributed around an elongated insert opening 402a. Such exemplary shaped cuts and gaps 401a distributed around the elongated insert opening 402a result in the bending-resistant insert member 400a to have a plurality of less bending-resistant portions around the infusion outlet port (e.g., 106 or 206). FIG. 4B shows a bending-resistant insert member 400b having a greater number of I-T-shaped slits 401b distributed around an elongated insert opening 402b. Such exemplary I- and T-shaped slits 401b distributed around the elongated insert opening 402b result in the bending-resistant insert member 400b to have a plurality of less bending-resistant portions around the infusion outlet port (e.g., 106 or 206). As illustrated, a greater number of smaller cuts or bending facilitating (i.e., less bending-resistant) portions, provided in the bending-resistant insert member, may be useful in order to possibly increase the size of an insert opening, while maintaining or even increasing the strength of the shaft portion around the proximal infusion outlet port (e.g., 106 or 206).

Another aspect of some embodiments of the present invention is a method of manufacturing an infusion balloon catheter. The herein disclosed manufacturing method is applicable to manufacturing any of the herein illustratively described exemplary embodiments of the infusion balloon catheter (and, components and features thereof), for example, infusion balloon catheter 100 or 200 (and, respective components and features thereof) shown in at least FIGS. 1A-1E, and in FIGS. 2A-2H, respectively.

FIG. 5 is a flow diagram of exemplary steps (procedures/processes) of an exemplary embodiment (indicated as, and referred to by, reference number 500), including the indicated exemplary steps (procedures/processes) thereof, of a method of manufacturing an infusion balloon catheter (such as that shown in the preceding figures). In FIG. 5, the exemplary embodiment 500 of the method includes exemplary steps (procedures/processes) represented by separate blocks (frames) which are assigned reference numbers, for example, 504, 508, 512, etc. As shown in FIG. 5, in a non-limiting manner, and in some embodiments, such as exemplary embodiment 500, the method of manufacturing an infusion balloon catheter includes the following exemplary steps (procedures/processes).

In 504, there is providing a multi-lumen shaft (e.g., 101 or 201) having a shaft wall enclosing at least a first lumen (e.g., 104 or 204) and a second lumen (e.g., 105 or 205) separated, and separately sealed, from each other by a dividing wall (e.g., 255 shown in FIG. 2E).

In 508, there is forming an infusion outlet port (e.g., 106 or 206) in proximity to a distal end (e.g., 103 or 203) of the shaft (101 or 201).

in 512, there is inserting into the second lumen (105 or 205) a bending-resistant insert member (e.g., 107 or 207; or any of 300a, 300b, 300c, 300d, 300e, 300f, 400a, and 400b) having at least one insert opening (e.g., 108 or 208; or any of 301a, 301b, 301c, 301d, 301e, 301f), in a manner such that the bending-resistant insert member conforms to the shape of the inner surface (e.g., 260 shown in FIG. 2D) of the shaft wall (e.g., 262 shown in FIG. 2D) with each lateral end (e.g., 257 and 258 shown in FIG. 2E) thereof extending to a junction line of the dividing wall (255) and the shaft wall (262), thereby preventing rotation of the bending-resistant insert member in the second lumen (105 or 205).

In 516, there is shifting the bending-resistant insert member into coincidence with the infusion outlet port (106 or 206), such that the at least one insert opening is in direct fluid communication with the infusion outlet port (106 or 206) at a seam formed via the coincidence.

In 520, there is affixing the bending-resistant insert member to the shaft wall (262), so as to prevent or minimize relative movement or shifting between the at least one insert opening and the infusion outlet port (106 or 206).

In exemplary embodiments of the infusion balloon catheter manufacturing method, step (process/procedure) 520 of affixing includes forming a proximal slide-prevention element (e.g., 120a shown in FIG. 1A; or 220a shown in FIG. 2D) adjacently proximal to the bending-resistant insert member (e.g., 107 or 207) and a distal slide-prevention element (e.g., 120b shown in FIG. 1A) adjacently distal to the bending-resistant insert member, thereby preventing or minimizing axial motion of the bending-resistant insert member in the second lumen (106 or 205). In exemplary embodiments, the affixing includes bonding the bending-resistant insert member (e.g., 107 or 207) to an inner surface (260) of the shaft wall (262) with a bonding agent. In exemplary embodiment, the bending-resistant insert member is coated with the bonding agent prior to the bonding.

Exemplary embodiments of the infusion balloon catheter manufacturing method further include connecting a balloon assembly (e.g., 264 shown in FIG. 2G), including an inflatable balloon member (102 or 202), to the distal end (103 or 203) of the shaft (101 or 201). In exemplary embodiments, the balloon assembly (264) includes an inner tube (e.g., 266 shown in FIGS. 2D, 2H) configured for passing a guidewire (GW), and the step (procedure) of connecting the balloon assembly (264) facilitates holding a proximal end (268) of the inner tube (266) extending in, and distally to, the second lumen (105 or 205), whereby the inner tube proximal end (268) is positioned and sized so as to prevent or minimize distal shifting of the bending-resistant insert member from the coincidence.

Exemplary embodiments of the infusion balloon catheter manufacturing method further include adding a heat shrink element about the shaft wall (262) proximally to the bending-resistant insert member, so as to prevent or minimize proximal shifting of the bending-resistant insert member from the coincidence.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the sated or described numerical range.

Moreover, for stating or describing a numerical range, the phrase 'in the range of between about a first numerical value and about a second numerical value', is considered equivalent to, and meaning the same as, the phrase 'in a range of from about a first numerical value to about a second numerical value', and, thus the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected', as used herein, equivalently refers to the corresponding synonymous phrases 'operatively joined', and 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extend that section headings are used, they should not be construed as necessarily limiting.

The invention claimed is:

1. An infusion balloon catheter comprising:
   an inflatable balloon member;
   a shaft having a distal end attached to said balloon member, the shaft having a shaft wall defining:
      a first lumen that provides passage to a balloon inflation fluid, and
      a second lumen that provides passage to an infusion fluid and a guidewire; and
   a bending-resistant insert member housed in said second lumen and located proximally to said balloon member, said bending-resistant insert member is axially fixed to and conforms to an inner surface of said shaft wall and defines at least one insert opening;
   wherein said shaft wall has an infusion outlet port located along, and providing an opening to, said second lumen proximally to said balloon member, said at least one insert opening is in direct fluid communication with said infusion outlet port, and said bending-resistant insert member provides structural support to a portion of said shaft wall surrounding said infusion outlet port and along a length extending between a point in proximity to a proximal end of said infusion outlet port and a point in proximity to a proximal end of said balloon member.

2. The balloon catheter of claim 1, wherein said first and second lumens are separated, and separately sealed, from each other by a dividing wall extending longitudinally along said shaft, such that said balloon inflation fluid passing through said first lumen is separated from said infusion fluid passing through said second lumen;
   wherein one of said first and second lumens has an oval shaped cross section, and the other of said first and second lumens has a crescent shaped cross section;
   wherein said bending-resistant insert member has lateral ends protruding away from said at least one insert opening towards said dividing wall.

3. The balloon catheter of claim 2, wherein said bending-resistant insert member abuts said inner surface of said shaft wall along most or all of an area of said inner surface that spans between said lateral ends of said bending-resistant insert member.

4. The balloon catheter of claim 2, wherein each of said lateral ends is adjacent to, or in contact with, a corresponding junction line of said dividing wall with said shaft wall, thereby holding said bending-resistant insert member in said second lumen so as to prevent rotation of said bending-resistant insert member around a long axis of said shaft.

5. The balloon catheter of claim 1, wherein said bending-resistant insert member is curved in accordance with a portion of a shape of said inner surface of said shaft wall, and housed in a dedicated section of said second lumen bordered with slide-prevention elements that prevent said bending-resistant insert member from proximally or distally sliding along said shaft.

6. The balloon catheter of claim 5, wherein at least one of said slide-prevention elements is formed by local constriction of said inner surface of said shaft wall.

7. The balloon catheter of claim 5, wherein at least one of said slide-prevention elements is an end portion of a tube lain at least partially across said second lumen.

8. The balloon catheter of claim 1, wherein said bending-resistant insert member is configured as a plate member made from at least one material selected from: stainless steel, aluminum, Co—Cr alloy, Ni—Ti alloy, and hard polymer.

9. The balloon catheter of claim 1, wherein said bending-resistant insert member has a length of about 5 mm and a thickness of about 0.03 mm.

10. The balloon catheter of claim 1, wherein said at least one insert opening and said infusion outlet port are configured to direct flow of said infusion fluid distally via an obtuse angle from about 110 degrees to about 150 degrees.

11. The balloon catheter of claim 1, wherein said at least one insert opening and said infusion outlet port are configured to direct an infusion outflow having a flow rate in a range of about 1 cm$^3$/sec to about 2 cm$^3$/sec.

12. The balloon catheter of claim 1, wherein said at least one insert opening is juxtaposed with said infusion outlet port.

13. The balloon catheter of claim 1, wherein said at least one insert opening is larger than said infusion outlet port.

14. The balloon catheter of claim 1, wherein said at least one insert opening is smaller than said infusion outlet port.

15. The balloon catheter of claim 1, wherein said infusion outlet port includes a single infusion opening having a cross sectional diameter from about 1 mm to about 2 mm.

16. The balloon catheter of claim 1, wherein a center point of said infusion outlet port is located 25 mm or less proximally to a closest point of said balloon member.

17. The balloon catheter of claim 1, wherein said at least one insert opening and said infusion outlet port define at least one through hole having a cross-sectional area greater by at least 0.5 mm$^2$ than an effective infusion lumen cross-sectional area.

18. The balloon catheter of claim 17, wherein said effective infusion lumen cross-sectional area is equal to or smaller than a minimum cross-sectional area of said second lumen proximally to said infusion outlet port, minus at least about 0.385 mm$^2$.

19. The balloon catheter of claim 17, wherein said cross-sectional area of said at least one through hole is from about 2 mm$^2$ to about 4 mm$^2$.

20. The balloon catheter of claim 17, wherein said cross-sectional area of said at least one through hole is greater than a cross-sectional area of an infusion inlet opening provided at a proximal end of said shaft wall and configured for direct fluid communication with an infusion fluid delivery apparatus.

21. The balloon catheter of claim 20, wherein said at least one through hole cross-sectional area is about 1.5 times greater than said cross-sectional area of said infusion inlet opening.

22. The balloon catheter of claim 20, wherein said at least one through hole cross-sectional area is greater by about 0.85 mm$^2$ than said cross-sectional area of said infusion inlet opening.

23. An infusion balloon catheter comprising:
an inflatable balloon member;
a shaft having a distal end attached to said balloon member, the shaft having a shaft wall defining:
a first lumen that provides passage to a balloon inflation fluid, and
a second lumen that provides passage to an infusion fluid and a guidewire; and
a bending-resistant insert member housed in said second lumen and located proximally to said balloon member, said bending-resistant insert member is affixed to and conforms to an inner surface of said shaft wall and defines at least one insert opening;
wherein said shaft wall has an infusion outlet port located along, and providing an opening to, said second lumen proximally to said balloon member, said at least one insert opening is in fluid communication with said infusion outlet port and is smaller than said infusion outlet port, and said bending-resistant insert member provides structural support to a portion of said shaft wall surrounding said infusion outlet port and along a length of said shaft wall defined between a point in proximity to a proximal end of said infusion outlet port and a point in proximity to a proximal end of said balloon member.

* * * * *